United States Patent
Arai et al.

(10) Patent No.: US 11,696,886 B2
(45) Date of Patent: Jul. 11, 2023

(54) COSMETIC

(71) Applicant: SHISEIDO COMPANY, LTD., Tokyo (JP)

(72) Inventors: Daiki Arai, Yokohama (JP); Hideki Shimizu, Yokohama (JP); Tetsuro Yonezawa, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/617,238

(22) PCT Filed: May 30, 2018

(86) PCT No.: PCT/JP2018/020802
§ 371 (c)(1),
(2) Date: Nov. 26, 2019

(87) PCT Pub. No.: WO2018/221606
PCT Pub. Date: Dec. 6, 2018

(65) Prior Publication Data
US 2021/0128445 A1    May 6, 2021

(30) Foreign Application Priority Data
May 31, 2017   (JP) ................. 2017-108469

(51) Int. Cl.
*A61K 8/06* (2006.01)
*A61K 8/86* (2006.01)
*A61Q 17/04* (2006.01)
*A61K 8/81* (2006.01)
*A61K 8/34* (2006.01)

(52) U.S. Cl.
CPC ............ *A61K 8/8164* (2013.01); *A61K 8/062* (2013.01); *A61K 8/342* (2013.01); *A61K 8/345* (2013.01); *A61K 8/8147* (2013.01); *A61K 8/8188* (2013.01); *A61K 8/86* (2013.01); *A61Q 17/04* (2013.01); *A61K 2800/522* (2013.01); *A61K 2800/591* (2013.01)

(58) Field of Classification Search
CPC ...... A61K 8/8164; A61K 8/062; A61K 8/342; A61K 8/345; A61K 8/8147; A61K 8/8188; A61K 8/86; A61K 2800/522; A61K 2800/591; A61Q 17/04
See application file for complete search history.

(56) References Cited

U.S. PATENT DOCUMENTS

| | | | | |
|---|---|---|---|---|
| 8,088,364 B2 * | 1/2012 | Breyfogle | ............... | A61P 31/00 424/59 |
| 9,180,074 B2 * | 11/2015 | Fukui | ..................... | A61K 8/37 |
| 10,835,460 B2 * | 11/2020 | Miyahara | ............. | B01J 13/0065 |
| 2012/0071568 A1 * | 3/2012 | Sugiyama | ................ | A61K 8/04 514/777 |
| 2012/0294912 A1 | 11/2012 | Fukui et al. | | |
| 2017/0105909 A1 * | 4/2017 | Miyahara | ............... | A61K 8/342 |
| 2017/0172858 A1 | 6/2017 | Ootake et al. | | |

FOREIGN PATENT DOCUMENTS

| | | |
|---|---|---|
| CN | 101657500 A | 2/2010 |
| CN | 102665656 A | 9/2012 |
| CN | 104936655 A | 9/2015 |
| CN | 106132388 A | 11/2016 |
| FR | 2924930 A1 | 12/2007 |
| JP | 2001-521880 | 11/2001 |
| JP | 2001-521880 A | 11/2001 |
| JP | 2005-068023 | 3/2005 |
| JP | 2008-222970 | 9/2008 |
| JP | 2008-222970 A | 9/2008 |
| JP | 2015182994 A * | 10/2015 ............. A61K 8/062 |
| JP | 2015221783 A * | 12/2015 |
| JP | 2016-020326 | 2/2016 |
| JP | 2016-20326 A | 2/2016 |
| JP | 2016-124860 | 7/2016 |
| JP | 2017-7969 | 1/2017 |
| JP | 2017-007969 A | 1/2017 |
| JP | 2017-57180 | 3/2017 |
| WO | WO 99/22698 | 5/1999 |
| WO | WO 2011/65439 | 6/2011 |
| WO | WO 2011/065439 A1 | 6/2011 |
| WO | WO 2014/111571 A1 | 7/2014 |
| WO | WO 2015/046390 A1 | 4/2015 |

OTHER PUBLICATIONS

Iwai, H. et al. International Journal of Cosmetic Science 20, 87-102 (1998) (Year: 1998).*
Patil, Anjali, and Robert W. Sandewicz. "Cosmetic science and polymer chemistry: Perfect together." Polymers for Personal Care and Cosmetics. American Chemical Society, 2013. 13-37 (Year: 2013).*
PCT/JP2018/020802 International Search Report (ISR) and Written Opinion (WO), dated Aug. 28, 2018 , 7 pages—English, 12 pages—Japanese.
European Patent Appln. No. EP 18809023.7, Extended Search Report dated Mar. 3, 2021, 8 pages—English.
JP 2019-521277, Notice of Reasons for Refusal, dated Jun. 20, 2022, 9 pages—English; 7 pages—Japanese.
CN 201880035076.4, Office Action dated Nov. 29, 2022, 8 pages—English, 9 pages—Chinese.

* cited by examiner

*Primary Examiner* — Mina Haghighatian
*Assistant Examiner* — Janice Y Silverman
(74) *Attorney, Agent, or Firm* — Andrew F. Young; Nolte Lackenbach Siegel

(57) ABSTRACT

Provided is a cosmetic having a unique soft and springy feeling in use, capable of stably formulating therein a UV protector, and providing a light feeling in use such that the cosmetic is separated into pieces when applied to the skin. The present invention relates to a cosmetic characterized by comprising (A) a (meth)acrylic acid/an alkyl (meth)acrylate/a (meth)acrylic acid-POE monoalkyl ether ester copolymer, (B) a UV protector, (C) a nonionic surfactant, and (D) a higher alcohol.

3 Claims, No Drawings

COSMETIC

CROSS REFERENCE TO RELATED APPLICATIONS

This application relates to and claims priority as a § 371 national phase, from PCT/JP2018/020802 filed May 30, 2018, the entire contents of which are incorporated herein by reference, which in turn claims priority from JP Ser. No.: 2017-108469 filed May 31, 2017.

FIGURE SELECTED FOR PUBLICATION

None

TECHNICAL FIELD

The present invention relates to a cosmetic. More specifically, the present invention relates to an oil-in-water emulsion cosmetic that provides a dewy feeling in use while having a uniquely soft texture in use, while also allowing an ultraviolet protectant to be stably blended therein.

BACKGROUND ART

In the development of cosmetics, for example, sunscreen cosmetics, ultraviolet protectants such as ultraviolet absorbing agents and ultraviolet scattering agents are appropriately combined and blended in order to efficiently screen (block) ultraviolet rays spanning from the UVA range to the UVB range. However, many of these ultraviolet protectants are blended into the oil phase, so many water-in-oil emulsion cosmetics are being developed as emulsions having high sunscreen effects and excellent stability.

However, in addition to the fact that many water-in-oil emulsion cosmetics are difficult to be easily washed away with normal detergents and soaps, there was also the problem of the feeling in use, such as a feeling of dryness occurring due to containing large quantities of ultraviolet protectants. Therefore, there is a desire for a cosmetic in the form of an oil-in-water emulsion that can be easily washed away, and that has a further improved feeling in use.

On the other hand, in oil-in-water emulsion cosmetics, acrylic polymers are used as thickeners in order to obtain an emulsion cosmetic that provides a soft texture while simultaneously lacking stickiness and having excellent spreadability on the skin (Patent Document 1). However, in systems in which such acrylic polymers were blended as emulsifiers, the stable blending of an ultraviolet protectant has not been realized.

RELATED ART

Patent Documents

Patent Document 1: JP 2005-68023 A

SUMMARY OF THE INVENTION

Problem to be Solved by the Invention

Thus, the problem to be addressed by the present invention is to provide a cosmetic having a uniquely soft texture in use, in which an ultraviolet protectant can be stably blended, and that also has an excellent feeling in use.

Means for Solving the Problem

The present inventors performed diligent research towards solving the above-mentioned problem, as a result of which they discovered that, by blending a (meth)acrylic acid/alkyl (meth)acrylate/(meth)acrylic acid-POE monoalkyl ether ester copolymer, as an emulsifier, into an oil-in-water emulsion containing an ultraviolet protectant, and introducing an α-gel structure, it is possible to obtain a cosmetic that provides excellent sunscreen effects, in which an ultraviolet protectant is stably blended, while having a uniquely soft texture in use, thereby completing the present invention.

In other words, the present invention provides a cosmetic characterized by containing:
(A) a (meth)acrylic acid/alkyl (meth)acrylate/(meth)acrylic acid-POE monoalkyl ether ester copolymer;
(B) an ultraviolet protectant;
(C) a non-ionic surfactant; and
(D) a higher alcohol.

Effects of the Invention

In the cosmetic of the present invention, it is possible to stably blend an ultraviolet protectant, thus providing high ultraviolet protection performance across a wide wavelength range. Furthermore, when applied to the skin, the cosmetic has a uniquely soft texture in use, has good spreadability, and provides a dewy feeling in use.

In the present specification, the "uniquely soft texture in use" refers to a texture (touch sensation) as if a bavarois (a gelatin jelly) in which, when the cosmetic is applied to the skin by the fingers, there is a lightness of application in which the viscosity suddenly drops as if collapsing, and the cosmetic is easy to spread, lacks stickiness and provides a dewy feeling in use.

MODES FOR CARRYING OUT THE INVENTION

The cosmetic of the present invention comprises (A) a (meth)acrylic acid/alkyl (meth)acrylate/(meth)acrylic acid-POE monoalkyl ether ester copolymer (hereinafter, sometimes referred to simply as "component (A)").

The (A) (meth)acrylic acid/alkyl (meth)acrylate/(meth)acrylic acid-POE monoalkyl ether ester copolymer used in the present invention is a copolymer of:
(a1) acrylic acid or methacrylic acid;
(a2) alkyl acrylate or alkyl methacrylate; and
(a3) an ester of acrylic acid or methacrylic acid with polyoxyethylene alkyl ether.

These are, for example, as listed in the ICID (International Cosmetic Ingredient Dictionary), acrylates/ceteth-20 methacrylate copolymer, acrylates/steareth-20 methacrylate copolymer, acrylates/steareth-25 methacrylate copolymer, acrylates/steareth-50 methacrylate copolymer, acrylates/beheneth-25 methacrylate copolymer, acrylates/steareth-20 methacrylate crosspolymer, ammonium acryloyldimethyltaurate/beheneth-25 methacrylate crosspolymer and the like, which are commercially available as aqueous dispersions (polymer emulsions).

The (A) (meth)acrylic acid/alkyl (meth)acrylate/(meth)acrylic acid-POE monoalkyl ether ester copolymer used in the cosmetic of the present invention is preferably selected from among acrylates/steareth-20 methacrylate copolymer (Aculyn 22; Rohm and Haas), acrylates/steareth-25 methacrylate copolymer (Aculyn 28; Rohm and Haas), acrylates/steareth-20 methacrylate crosspolymer (Aculyn 88; Rohm and Haas) and ammonium acryloyldimethyltaurate/beheneth-25 methacrylate crosspolymer (Aristoflex HMB; Clariant Production UK Ltd.). Among these, it is particularly preferable to use acrylates/steareth-20 methacrylate copolymer or acrylates/steareth-20 methacrylate crosspolymer.

An aqueous dispersion of the above-mentioned acrylic acid-based polymer is diluted with water or the like as needed, and an alkaline agent is added for neutralization, thereby increasing its viscosity. The copolymer-neutralizing alkaline agent is not particularly limited, and an inorganic base such as sodium hydroxide or potassium hydroxide, triethanolamine or isopropanolamine, or an organic base such as a basic amino acid or the like may be used.

The blended amount of the component (A) in the cosmetic of the present invention should be 0.01 to 3.0% by mass, preferably 0.05 to 2.0% by mass, more preferably 0.1 to 1.4% by mass, and even more preferably 0.3 to 1.0% by mass, by actual polymer content relative to the overall mass of the cosmetic. If the blended amount is less than 0.01% by mass, then emulsion stability is not obtained, and if more than 3.0% by mass is blended, then the properties when used may be made worse, such as by the makeup deteriorating after application.

The cosmetic of the present invention comprises a (B) ultraviolet protectant (hereinafter, sometimes referred to as "component (B)"). The ultraviolet protectant may be an ultraviolet absorbing agent or an ultraviolet scattering agent, respectively used alone, or an ultraviolet absorbing agent and an ultraviolet scattering agent used in combination.

The ultraviolet absorbing agent used in the present invention is not particularly limited, but a broad range of ultraviolet absorbing agents that are generally used in cosmetics may be given as examples. Examples include benzoic acid derivatives, salicylic acid derivatives, cinnamic acid derivatives, dibenzoylmethane derivatives, β,β-diphenyl acrylate derivatives, benzophenone derivatives, benzylidene camphor derivatives, phenylbenzimidazole derivatives, triazine derivatives, phenylbenzotriazole derivatives, anthranil derivatives, imidazoline derivatives, benzalmalonate derivatives, 4,4-diaryl butadiene derivatives and the like. Hereinafter, specific examples and product names will be mentioned, but there is no limitation thereto.

Examples of benzoic acid derivatives include ethyl para-aminobenzoate (PABA), ethyl-dihydroxypropyl PABA, ethylhexyl-dimethyl PABA, glyceryl PABA, PEG-25-PABA and diethylamino hydroxybenzoyl hexyl benzoate.

Examples of salicylic acid derivatives include homosalate, ethylhexyl salicylate, dipropylene glycol salicylate and TEA (triethanolamine) salicylate.

Examples of cinnamic acid derivatives include octyl methoxycinnamate or ethylhexyl methoxycinnamate, isopropyl methoxycinnamate, isoamyl methoxycinnamate, cinnoxate, DEA (diethanolamine) methoxycinnamate, diisopropyl methylcinnamate, glyceryl ethylhexanoate dimethoxycinnamate, and di-(2-ethylhexyl)-4'-methoxybenzalmalonate.

Examples of dibenzoyl methane derivatives include 4-tert-butyl-4'-methoxy dibenzoyl methane.

Examples of β, β-diphenyl acrylate derivatives include octocrylene.

Examples of benzophenone derivatives include benzophenone-1, benzophenone-2, benzophenone-3 or oxybenzone, benzophenone-4, benzophenone-5, benzophenone-6, benzophenone-8, benzophenone-9 and benzophenone-12.

Examples of benzylidene camphor derivatives include 3-benzylidene camphor, 4-methylbenzylidene camphor, benzylidene camphor sulfonic acid, camphor benzalkonium methosulfate, terephthalylidene dicamphor sulfonic acid and polyacrylamide methylbenzylidene camphor.

Examples of phenylbenzimidazole derivatives include phenylbenzimidazole sulfonic acid and disodium phenyldibenzimidazole tetrasulfonate.

Examples of triazine derivatives include bis-ethylhexyloxyphenyl methoxyphenyl triazine, ethylhexyl triazone, diethylhexyl butamido triazone, 2,4,6-tris(diisobutyl-4'-aminobenzalmalonate)-s-triazine and 2,4,6-tris[4-(2-ethylhexyloxycarbonyl)anilino]-1,3,5-triazine.

Examples of phenylbenzotriazole derivatives include drometrizole trisiloxane and methylene bis(benzotriazolyl tetramethylbutyl phenol).

Examples of anthranil derivatives include menthyl anthranilate.

Examples of imidazoline derivatives include ethylhexyl dimethoxybenzylidene dioxoimidazoline propionate.

Examples of benzalmalonate derivatives include polyorganosiloxanes having benzalmalonate functional groups (e.g. Polysilicone 15).

Examples of 4,4-diarylbutadiene derivatives include 1,1-dicarboxy (2,2'-dimethylpropyl)-4,4-diphenylbutadiene.

The ultraviolet absorbing agent used in the present invention may be of one type or a combination of two or more types. In the present invention, in order to further increase the ultraviolet protection performance, it is preferable to combine and blend at least a solid oil-soluble ultraviolet absorbing agent. Examples of solid oil-soluble ultraviolet absorbing agents include diethylamino hydroxybenzoyl hexyl benzoate, bis-ethylhexyloxyphenol methoxyphenyl triazine, ethylhexyl triazone and the like.

Normally, solid oil-soluble ultraviolet absorbing agents are highly polar, so blending them into emulsion cosmetics reduces the stability. However, in the system used in the present invention, it is possible to stably blend a solid oil-soluble ultraviolet absorbing agent.

The ultraviolet scattering agent used in the present invention is not particularly limited, but an example is a zinc oxide or titanium oxide powder.

The zinc oxide and the titanium oxide used in the present invention may be of a type that can normally be blended into cosmetics as ultraviolet scattering agents. For example, a zinc oxide or a titanium oxide (dioxide) in which the average particle size of primary particles is 0.005 μm or larger is preferably used. The average particle size in the present specification refers to the average particle size of primary particles of the ultraviolet scattering agent in the final formulation (if the particles are individually dispersed, then those particles; if they are present as clustered aggregate particles, then those aggregate particles). This average particle size is preferably in the range 0.01 μm to 10 μm, more preferably 0.02 μm to 1 μm, and most preferably 0.02 μm to 0.1 μm. For example, a pigment-grade ultraviolet scattering agent having an average particle size of 0.1 to 1 μm or fine particles having an average particle size of 0.02 to 0.06 μm is preferred.

Additionally, an ultraviolet scattering agent having a hydrophobic surface, in which the surface of a substrate such as zinc oxide or titanium oxide has been hydrophobically treated, is used.

Examples of the surface hydrophobic treatment method include silicone treatments such as those using methyl hydrogen polysiloxane, methyl polysiloxane and methyl phenyl polysiloxane; fluorine treatments such as those using perfluoroalkyl phosphoric acid esters and perfluoroalcohols; amino acid treatments such as those using N-acylglutamic acid; lecithin treatments; metal soap treatments such as those using aluminum stearate, calcium stearate and magnesium stearate; fatty acid treatments such as those using palmitic acid, isostearic acid, stearic acid, lauric acid, myristic acid, behenic acid, oleic acid, rosin acid and 12-hydroxystearic acid; alkyl phosphoric acid ester treatments; alkoxysilane treatments such as those using methyltrimethoxysilane, ethyltrimethoxysilane, hexyltrimethoxysilane, octyltrimethoxysilane and octyltriethoxysilane; fluoroalkylsilane treatments such as those using trifluoromethylethyltrimethoxysilane and heptadecafluorodecyltrimethoxysilane; fatty acid ester treatments such as those using dextrin fatty acid esters, cholesterol fatty acid esters, sucrose fatty acid esters and starch fatty acid esters; and silica treatments.

The blended amount of the component (B) in the cosmetic of the present invention should be 1.0 to 30% by mass, preferably 3.0 to 25% by mass, more preferably 5.0 to 20% by mass relative to the overall mass of the cosmetic. If the blended amount is less than 1.0% by mass, then sufficient ultraviolet protection effects cannot be obtained, and if more than 30.0% by mass is blended, then the emulsion stability and the usage properties may sometimes be reduced.

The cosmetic of the present invention comprises a (C) non-ionic surfactant (hereinafter, sometimes referred to simply as "component (C)").

The (C) non-ionic surfactant used in the cosmetic of the present invention is not particularly limited. Specific examples include polyethylene glycol fatty acid esters, polyoxyethylene glyceryl fatty acids, polyoxyethylene behenyl ethers, polyoxyethylene polyoxypropylene alkyl ethers, polyethylene hydrogenated castor oil, polyoxyethylene/methylpolysiloxane copolymers, polyoxyethylene sorbitol fatty acids, polyoxyethylene alkyl ethers, maltitol hydroxy aliphatic alkyl ethers, alkylated polysaccharides, alkylglucosides, sucrose fatty acid esters, polyoxyethylene glyceryl hydrogenated castor oil, polyoxyethylene sorbitan fatty acid esters, polyoxyethylene/polyoxypropylene block copolymers, tetrapolyoxyethylene/tetrapolyoxypropylene-ethylene diamine condensates, polyoxyethylene-beeswax/lanolin derivatives, alkanolamides, polyoxyethylene-propylene glycol fatty acid esters, polyoxyethylene-alkylamines, polyoxyethylene-fatty acid amides, alkylethoxydimethylamine oxides, trioleylphosphoric acid, and the like. One or more types of non-ionic surfactants may be used. Examples of the (C) non-ionic surfactant of the present invention include hydrophilic non-ionic surfactants having an HLB of 8 or higher such as, for example, polyoxyethylene (10-50) behenyl ethers such as beheneth-20, polyoxyethylene (20-60) sorbitan monostearates such as polysorbate-60, polyoxyethylene (10-80) glyceryl fatty acids such as PEG-60 glyceryl isostearate, polyoxyethylene (10-50) polyoxypropylene (2-30) cetyl ethers such as PPG-8 ceteth-20, polyoxyethylene (20-100) hydrogenated castor oils such as PEG-60 hydrogenated castor oil, and polyethylene glycol monostearates such as PEG-40 stearate. Among the above, it is preferable to use one or more of polyoxyethylene (10-50) behenyl ether, polyoxyethylene (20-60) sorbitan monostearate, polyoxyethylene (10-50) polyoxypropylene (2-30) cetyl ether and polyoxyethylene (20-100) hydrogenated castor oil. Furthermore, in the cosmetic of the present invention, a polyoxyethylene behenyl ether is preferred, a polyoxyethylene behenyl ether in which the average number of moles of ethylene oxide added is 20 to 40 is more preferred, and beheneth-20 is even more preferred.

The blended amount of the component (C) in the cosmetic of the present invention should preferably be 0.1 to 10% by mass, more preferably 0.2 to 5.0% by mass, and even more preferably 0.3 to 2.0% by mass relative to the overall mass of the cosmetic. If the blended amount is less than 0.1% by mass or more than 10% by mass, then sufficient emulsion stability may sometimes not be able to be obtained.

The cosmetic of the present invention comprises a (D) higher alcohol (hereinafter, sometimes referred to simply as "component (D)").

The (D) higher alcohol used in the cosmetic of the present invention is not particularly limited as long as it is a higher alcohol having 6 or more carbon atoms that can be used in fields such as cosmetic products, pharmaceutical products and quasi-drug products, and includes saturated linear monohydric alcohols, unsaturated monohydric alcohols, and the like.

Examples of saturated linear monohydric alcohols include dodecanol (lauryl alcohol), tridodecanol, tetradodecanol (myristyl alcohol), pentadecanol, hexadecanol (cetyl alcohol), heptadecanol, octadecanol (stearyl alcohol), nonadecanol, icosanol (arachyl alcohol), heneicosanol, docosanol (behenyl alcohol), tricosanol, tetracosanol (carnaubyl alcohol), pentacosanol, hexacosanol (ceryl alcohol), and the like.

Examples of unsaturated monohydric alcohols include elaidyl alcohol and the like. In the present invention, saturated linear monohydric alcohols are preferable for the purpose of stability over time.

As the higher alcohol in the present invention, it is possible to use one or a combination of two or more of the above-mentioned types. In the present invention, it is preferable to use a monohydric aliphatic alcohol having 16 to 22 carbon atoms. In the present invention, when using a plurality of higher alcohols, mixtures of combinations such that the melting point of the mixture is 60° C. or higher are particularly preferred for the purpose of stability.

The blended amount of the component (D) in the cosmetic of the present invention should preferably be 0.1 to 10% by mass, more preferably 0.2 to 5.0% by mass, and even more preferably 0.2 to 3.0% by mass relative to the overall mass of the cosmetic. If the blended amount is less than 0.1% by mass or more than 10% by mass, then sufficient emulsion stability may sometimes not be able to be obtained.

The cosmetic of the present invention is an oil-in-water emulsion, containing water in the external phase. In the present invention, the (D) higher alcohol forms, together with the (C) non-ionic surfactant and the (E) water, an aggregate (also known as an "α-gel") having a lamellar liquid-crystal structure.

In the present invention, in order to further raise the emulsion stability, it is preferable to set the blending ratio ((C)/(D)) between the (C) non-ionic surfactant and the (D) higher alcohol to be 0.1 to 0.5 by molar ratio. Additionally, in order to similarly raise the emulsion stability, it is preferable to set the blending ratio ((A)/{(C)+(D)}) of the (A) (meth)acrylic acid/alkyl (meth)acrylate/(meth)acrylic acid-POE monoalkyl ether ester copolymer with respect to the (C) non-ionic surfactant and (D) higher alcohol to be 0.01 to 2.0 by % by mass.

In addition to components (A) to (D) above, the cosmetic of the present invention may further contain an oil other than the (E) higher alcohol.

As oils other than the (E) higher alcohol, it is possible to select any from among those generally used in cosmetic products, within a range not compromising the stability. Desirable oils include liquid oils/fats, solid oils/fats, waxes, hydrocarbon oils, higher fatty acids, ester oils, silicone oils and the like. Oils that are entirely liquid at 25° C. are suitable.

Examples of liquid oils/fats include avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, perilla oil, soybean oil, peanut oil, tea seed oil, Japanese torreya seed oil, rice bran oil, *Paulownia fargesii* oil, *Paulownia tomentosa* oil, jojoba oil, germ oil, triglycerin and the like.

Examples of solid oils/fats include cacao butter, coconut oil, horse fat, hydrogenated coconut oil, palm oil, beef tallow, mutton tallow, hydrogenated beef tallow, palm kernel oil, lard, beef bone fat, *Toxicodendron succedaneum* kernel oil, hydrogenated oil, neatsfoot oil, Japan wax, hydrogenated castor oil and the like.

Examples of waxes include beeswax, candelilla wax, cotton wax, carnauba wax, bayberry wax, insect wax, spermaceti, montan wax, rice bran wax, lanolin, kapok wax, lanolin acetate, liquid lanolin, sugarcane wax, lanolin fatty acid isopropyl ester, hexyl laurate, reduced lanolin, jojoba wax, hydrogenated lanolin, shellac wax, POE lanolin alcohol ether, POE lanolin alcohol acetate, POE cholesterol ether, lanolin fatty acid polyethylene glycol, POE hydrogenated lanolin alcohol ether and the like.

Examples of hydrocarbon oils include liquid paraffin, ozokerite, squalane, pristane, paraffin, ceresin, squalene, Vaseline®, microcrystalline wax and hydrogenated polydecene.

Examples of higher fatty acids include lauric acid, myristic acid, palmitic acid, stearic acid, behenic acid, oleic acid, undecylenic acid, toluic acid, isostearic acid, linolic acid, linoleic acid, eicosapentaenoic acid (EPA), docosahexaeneoic acid (DHA) and the like.

Examples of synthetic ester oils include isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythrityl tetra-2-ethylhexanoate, glycerin tri-2-ethylhexanoate, glycerin trioctanoate, glycerin triisopalmitate, trimethylolpropane triisostearate, cetyl 2-ethylhexanoate, 2-ethylhexyl palmitate, glycerin trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid 2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate and the like.

Examples of silicone oils include chain polysiloxanes (such as, for example, dimethylpolysiloxane, methylphenylpolysiloxane and diphenylpolysiloxane), cyclic polysiloxanes (such as, for example, octamethylcyclotetrasiloxane, decamethylcyclopentasiloxane and dodecamethylcyclohexasiloxane), silicone resins that form a three-dimensional mesh structure, silicone rubber, various types of modified polysiloxanes (amino-modified polysiloxane, polyether-modified polysiloxane, alkyl-modified polysiloxane, fluorine-modified polysiloxane and the like) and the like.

As the oil other than the (E) higher alcohol in the present invention, it is possible to use one or a combination of two or more of the above-mentioned types. In the present invention, it is possible to use a combination of two or more oils selected from among hydrocarbon oils, ester oils and silicone oils.

When an oil other than an (E) higher alcohol is blended into the present invention, the blended amount thereof should preferably be 1.0 to 20% by mass, more preferably 5.0 to 15% by mass relative to the overall mass of the cosmetic. If the blended amount is less than 1.0% by mass, then precipitation of the ultraviolet absorbing agent or reduction of the compatibility of the oil is observed, and if more than 20% by mass is blended, then the emulsion stability and the usage properties may sometimes be reduced.

It is possible to blend other arbitrary components that can normally be blended into cosmetics or quasi-drugs into the emulsion cosmetic of the present invention, within a range not inhibiting the effects of the present invention. The other arbitrary components are not limited, but may, for example, be powder components other than ultraviolet scattering agents, colorants, humectants, aqueous thickeners, dispersing agents, preservatives, fragrances and various medicinal agents.

Examples of powder components other than ultraviolet scattering agents include extender pigments such as talc, mica and kaolin, and polymer powders such as polyethylene powder, poly methyl methacrylate powder and nylon powder.

Examples of humectants include polyhydric alcohols such as glycerin, 1,3-butylene glycol, dipropylene glycol and propylene glycol, and water-soluble polymers such as trehalose, hyaluronic acid and chondroitin sulfate.

Examples of aqueous thickeners include succinoglycan, (dimethylacrylamide/sodium acryloyldimethyl taurate) crosspolymers, cellulose gum, carboxyvinyl polymers, xanthan gum and (hydroxyethyl acrylate/sodium acryloyldimethyl taurate) copolymers.

The cosmetic of the present invention may be produced in accordance with conventional methods for producing oil-in-water emulsion cosmetics such as, for example, by separately mixing the components constituting the oil phase and the components constituting the water phase, adding the oil phase to the water phase, and emulsifying.

The cosmetic of the present invention may be provided in the form of cosmetics in various forms, such as a liquid, a milky lotion, a cream, a gel or a bavarois-like form, among which a bavarois-like form is particularly preferred.

The cosmetic of the present invention may be provided as a skin-care cosmetic, a sunscreen cosmetic, a colorant-blended cosmetic, a foundation, a cosmetic base or a BB cream.

The emulsion cosmetic of the present invention has the dewy texture in use that is characteristic of oil-in-water emulsions, and further provides a uniquely soft texture in use due to the blending of the (meth)acrylic acid/alkyl (meth)acrylate/(meth)acrylic acid-POE monoalkyl ether ester copolymer. Furthermore, the ultraviolet protectant can be stably blended into the oil phase by introducing an α-gel structure, so excellent ultraviolet protection effects are obtained across a wide wavelength range from the UVA range to the UVB range.

EXAMPLES

Hereinafter, the present invention will be explained in further detail by providing examples, but the present invention is not limited by these examples in any way. Where not specially noted, the blended amounts are in % by mass relative to the total mass of the composition in which the relevant components are blended.

Oil-in-water emulsion cosmetics were prepared with the formulations indicated in Table 1 below. The cosmetics (samples) in each of the examples were evaluated for stability, texture, form and sense of collapse.
(1) Stability
After preparation, each sample was left for one week at room temperature or 50° C.,
and the states of the emulsions were evaluated.
Evaluation Criteria
A: Homogeneously emulsified at both room temperature and at 50° C.
B: Homogeneous at room temperature, but slight separation is observed when left at 50° C.
C: Separation is observed at any of room temperature and 50° C.
(2) Texture
After preparation, the texture of the cosmetic was evaluated.
Evaluation Criteria:
A: Soft, resilient texture (touch sensation) like a bavarois (a gelatin jelly).
B: Slightly resilient texture.
C: Texture like common cream or milky lotion.
(3) Form
After preparation, the form of the cosmetic was evaluated.
Evaluation Criteria:
A: Did not run down even when tilted, and liquid surface became flat after deformation.
B: Ran down slightly when tilted, or after deformation, liquid surface became slightly flat.
C: Ran down when tilted.
(4) Sense of Collapse
After preparation, the sense of collapse was evaluated by means of the loss tangent (tan δ) in a dynamic viscoelasticity measurement. As the apparatus, Physica MCR 301 rheometer, Anton Paar Japan K.K., was used, and a cone plate was used as the measurement tool. As the measurement conditions, the strain amplitude γ was set to 0.05% to 5,000% (logarithmically increasing), the frequency was f=1 Hz, the number of measurement points was 60, and the measurement interval was 1 s. The loss tangent (tan δ) is represented by dynamic loss (G")/storage modulus (G'). The greater the variation rate (slope) of tan δ, the greater the variation rate (sense of collapse) from an elastic body to a viscous body, as a result of which the sense of application becomes lighter. The slope of tan δ at each point was determined and the maximum value thereof was determined by the criteria below to evaluate the sense of collapse.
Evaluation Criteria:
A: the maximum value for the slope of tan δ was 1.5 or greater
B: the maximum value for the slope of tan δ was from 1 to less than 1.5
C: the maximum value for the slope of tan δ was less than 1.0

TABLE 1

| | | Ex. 1 | Ex. 2 | Ex. 3 | Comp. Ex. 1 | Comp. Ex. 2 |
|---|---|---|---|---|---|---|
| | Ion-exchanged water | bal | bal | bal | bal | bal |
| Component A | (Acrylates/steareth-20 methacrylate) copolymer | 0.6 | 0.6 | 0.6 | 0.6 | — |
| | Sodium lauryl sulfate | 0.003 | 0.003 | 0.003 | 0.003 | — |
| Component B | Ethylhexyl methoxycinnamate | 9.0 | 9.0 | 9.0 | 9.0 | 9.0 |
| | Oxybenzone-3 | 1.0 | 1.0 | 1.0 | 1.0 | 1.0 |
| | bis-Ethylhexyloxyphenol methoxyphenyl triazine | 1.0 | 1.0 | 1.0 | 1.0 | 1.0 |
| | Octocrylene | 3.0 | 3.0 | — | 3.0 | 3.0 |
| | Homosalate | — | — | 3.0 | — | — |
| | Phenylbenzimidazole sullbnate | — | — | 2.0 | — | — |
| | Titanium oxide | — | 1.0 | — | — | — |
| Component C | Beheneth-20 | 0.7 | 0.7 | 0.7 | — | 0.7 |
| Component D | Stearyl alcohol | 0.7 | 0.7 | 0.7 | — | 0.7 |
| | Behenyl alcohol | 0.8 | 0.8 | 0.8 | — | 0.8 |
| | Ethanol | 7.0 | 7.0 | 7.0 | 7.0 | 7.0 |
| | Glycerin | 2.0 | 2.0 | 2.0 | 2.0 | 2.0 |
| | Dipropylene glycol | 4.0 | 4.0 | 4.0 | 4.0 | 4.0 |
| | Hydrogenated polydecene | 3.0 | 3.0 | 3.0 | 3.0 | 3.0 |
| | Dimethicone | 2.0 | 2.0 | 2.0 | 2.0 | 2.0 |
| | Cyclopentasiloxane | 5.0 | 5.0 | 5.0 | 5.0 | 5.0 |
| | Diisopropyl sebacate | 1.5 | 1.5 | 1.5 | 1.5 | 1.5 |
| | Xanthan gum | — | — | 0.05 | 0.05 | 0.05 |
| | 4-Methoxysalicylic acid potassium salt | 1.0 | 1.0 | — | 1.0 | 1.0 |
| | Triethanolamine | 0.5 | 0.5 | 2.5 | 0.5 | 0.5 |
| | Chelating agent | s.a. | s.a. | s.a. | s.a. | s.a. |
| | Fragrance | s.a | s.a. | s.a. | s.a. | s.a. |
| | Total | 100.0 | 100.0 | 100.0 | 100.0 | 100.0 |
| Component (C)/component (D) blending ratio (molar ratio) | | 0.12 | 0.12 | 0.12 | — | 0.12 |
| Component (A)/{component (C) + component (D)} blending ratio (mass %) | | 0.3 | 0.3 | 0.3 | — | — |
| Evaluation | (1) Stability | A | A | A | C | A |
| | (2) Texture | A | A | A | C | C |
| | (3) Form | A | A | A | C | B |
| | (4) Sense of collapse (tan δ) | A | A | A | C | B |

When the (C) non-ionic surfactant and the (D) higher alcohol of the present invention were not contained (Comparative Example 1), the cosmetic did not have a bavarois-like form, and the stability, texture and sense of collapse were all inferior. Additionally, when the (A) (meth)acrylic acid/alkyl (meth)acrylate/(meth)acrylic acid-POE monoalkyl ether ester copolymer was not contained (Comparative Example 2), the bavarois-like shape (like a gelatin jelly) was not able to be sufficiently maintained, and a soft texture and sufficient sense of collapse were not able to be obtained. In comparison to these comparative examples, the cosmetics of the present invention (Examples 1 to 3) had a bavarois-like form, and had very good stability, texture and sense of collapse.

Furthermore, oil-in-water emulsion cosmetics were prepared with the formulations indicated in Table 2 below, and similarly evaluated for stability, texture, form and sense of collapse.

TABLE 2

| Type | Ingredient | Ex. 4 | Ex. 5 | Ex. 6 | Ex. 7 | Ex. 8 | Ex. 9 | Ex. 10 | Ex. 11 |
|---|---|---|---|---|---|---|---|---|---|
| Water | Water | bal | bal | bal | bal | bal | bal | bal | bal |
| Component A | (Acrylates/steareth-20 methacrylate) copolymer | — | 0.6 | — | — | — | 0.6 | 0.6 | 0.6 |
| | (Acrylates/steareth-25 methacrylate) copolymer | 0.6 | — | 0.6 | — | — | — | — | — |
| | (Acrylates/steareth-20 methacrylate) crosspolymer | — | — | — | 0.6 | — | — | — | — |
| | (Ammonium acryloyldimethyl taurate/beheneth-25 methacrylate) crosspolymer | — | — | — | — | 0.5 | — | — | — |
| | Xanthan gum | 0.1 | 0.1 | 0.1 | 0.1 | 0.1 | 0.1 | 0.1 | 0.1 |
| Humectant | Glycerin | 2.0 | 2.0 | 2.0 | 2.0 | 2.0 | 2.0 | 2.0 | 2.0 |
| | Dipropylene glycol | 4.0 | 4.0 | 4.0 | 4.0 | 4.0 | 4.0 | 4.0 | 4.0 |
| Component C | Beheneth-20 (HLB: 14) | 0.7 | 0.7 | 0.7 | 0.7 | 0.7 | — | — | — |
| | Polysorbate 60 (HLB: 15) | — | — | — | — | — | 0.7 | — | — |
| | PPG-8 ceteth-20 (HLB: 12.5) | — | — | — | — | — | — | 1.0 | — |
| | PEG-60 hydrogenated castor oil (HLB: 14) | — | — | — | — | — | — | — | 1.7 |
| Component D | Stearyl alcohol | 0.4 | 0.4 | 0.4 | 0.4 | 0.4 | 0.4 | 0.4 | 0.4 |
| | Behenyl alcohol | 0.9 | 0.9 | 0.9 | 0.9 | 0.9 | 0.9 | 0.9 | 0.9 |
| Neutralizer | Triethanolamine | 0.5 | 0.2 | 0.5 | 0.2 | 0.2 | 0.2 | 0.2 | 0.2 |
| Oil | Hydrogenated polydecene | 3.0 | 3.0 | 3.0 | 3.0 | 3.0 | 3.0 | 3.0 | 3.0 |
| | Dimethicone | 2.0 | 2.0 | 2.0 | 2.0 | 2.0 | 2.0 | 2.0 | 2.0 |
| | Cyclopentasiloxane | 5.0 | 5.0 | 5.0 | 5.0 | 5.0 | 5.0 | 5.0 | 5.0 |
| Component B | Ethylhexyl methoxycinnamate | 9.0 | 9.0 | 9.0 | 9.0 | 9.0 | 9.0 | 9.0 | 9.0 |
| | bis-Ethylhexyloxyphenol methoxyphenyl triazine | 1.0 | 1.0 | 1.0 | 1.0 | 1.0 | 1.0 | 1.0 | 1.0 |
| | Ethylhexyl triazone | 0.5 | 0.5 | 0.5 | 0.5 | 0.5 | 0.5 | 0.5 | 0.5 |
| Alcohol | Ethanol | 7.0 | 7.0 | 7.0 | 7.0 | 7.0 | 7.0 | 7.0 | 7.0 |
| Powder | Silica | 2.0 | 2.0 | 2.0 | 2.0 | 2.0 | 2.0 | 2.0 | 2.0 |
| Medicinal agent | 4-Methoxysalicylic acid potassium salt | — | 1.0 | 1.0 | 1.0 | 1.0 | 1.0 | 1.0 | 1.0 |
| Other | Stabilizer/fragrance | s.a. | s.a. | s.a. | s.a. | s.a. | s.a. | s.a. | s.a. |
| | Total | 100.0 | 100.0 | 100.0 | 100.0 | 100.0 | 100.0 | 100.0 | 100.0 |
| | Component (C)/component (D) blending ratio (molar ratio) | 0.14 | 0.14 | 0.14 | 0.14 | 0.14 | 0.21 | 0.15 | 0.11 |
| | Component (A)/{component (C) + component (D)} blending ratio (mass %) | 0.30 | 0.30 | 0.30 | 0.30 | 0.25 | 0.30 | 0.26 | 0.20 |
| Evaluation | (1) Stability | A | A | A | A | A | A | A | A |
| | (2) Texture | A | A | A | A | A | A | A | A |
| | (3) Form | A | A | A | A | A | A | A | A |
| | (4) Sense of collapse (tan δ) | A | A | A | A | A | A | B | C |

The cosmetics of Examples 4 to 11 above all were able to stably blend an ultraviolet protectant, had a bavarois-like form, and had a good texture and feeling in use. Although there was a tendency for the cosmetic in Example 11 to feel heavy when applied, it was of a level that would not pose any problems in actual use.

Hereinafter, other formulation examples of the cosmetic according to the present invention are indicated. All of the formulations had excellent emulsion stability, had a uniquely soft texture in use, were able to be spread on the skin and had a dewy feeling in use.

TABLE 3

| Ingredients | Form. Ex. 1 | Form. Ex. 2 | Form. Ex. 3 | Form. Ex. 4 | Form. Ex. 5 |
|---|---|---|---|---|---|
|  | Sunscreen lotion | Sunscreen | Sunscreen | BB cream | Skin-care cream |
| Water | bal | bal | bal | bal | bal |
| (Acrylates/steareth-20 methacrylate) copolymer | 1.2 | 0.2 | 0.6 | 0.2 | 0.6 |
| Carbomer | — | — | — | 0.1 | 0.1 |
| Xanthan gum | 0.1 | 0.1 | — | — | 0.05 |
| Sodium carboxymethyl cellulose | — | — | 0.1 | 0.05 | — |
| Glycerin | 2.0 | 2.0 | 2.0 | 2.0 | 2.0 |
| Dipropylene glycol | 4.0 | 4.0 | 4.0 | 4.0 | 4.0 |
| PEG-10 dimethicone | — | — | — | — | 0.2 |
| Beheneth-20 | 0.7 | 0.7 | — | 0.7 | 1.0 |
| PEG-60 hydrogenated castor oil | — | — | 2.0 | — | — |
| Stearyl alcohol | 0.4 | 0.7 | 0.7 | 0.5 | 0.5 |
| Behenyl alcohol | 1.0 | 1.0 | 1.0 | 1.0 | 1.5 |
| Triethanolamine | 0.5 | 2.3 | 2.0 | 0.5 | 0.5 |
| Hydrogenated polydecene | 3.0 | 3.0 | 3.0 | 3.0 | 1.0 |
| Liquid paraffin | — | — | — | — | 3.0 |
| Methylpolysiloxane | — | — | — | — | 4.0 |
| Dimethicone | 2.0 | 2.0 | 2.0 | 2.0 | 2.0 |
| Cyclopentasiloxane | 5.0 | 5.0 | 5.0 | 5.0 | 5.0 |
| Diisopropyl sebacate | — | 1.5 | — | 1.5 | 7.0 |
| Ethylhexyl methoxycinnamate | 9.0 | 9.0 | 9.0 | 9.0 | 1.0 |
| Octocrylene | — | — | — | 3.0 | — |
| Homosalate | — | 3.0 | — | — | — |
| Polysilicone-15 | 0.5 | — | 0.5 | — | — |
| Oxybenzone-3 | — | 1.0 | — | — | — |
| bis-Ethylhexyloxyphenol methoxyphenyl triazine | 1.0 | 1.0 | 1.0 | 1.0 | — |
| Diethylamino hydroxybenzoyl hexyl benzoate | — | — | — | — | 0.5 |
| Ethylhexyl triazone | 0.5 | — | 0.5 | — | — |
| Terephthalylidene dicamphor sulfonic acid | — | 0.5 | — | — | — |
| Phenylbenzimidazole sulfonic acid | — | 2.0 | — | — | — |
| Polyoxyethylene (14) polyoxypropylene (7) dimethyl ether | — | 0.5 | — | — | — |
| Stearic acid | — | 0.5 | — | — | — |
| Ethanol | 7.0 | 7.0 | 7.0 | 7.0 | 7.0 |
| Titanium oxide | — | — | — | 2.2 | — |
| Hydrophobically treated fine particle zinc oxide | — | — | 4.0 | — | — |
| Iron oxide | — | — | — | 0.8 | — |
| Mica | — | — | — | 0.4 | — |
| Silica | 2.0 | 1.0 | 2.0 | — | 0.5 |
| Talc | — | — | — | 1.0 | — |
| 4-Methoxysalicylic acid potassium salt | — | — | 1.0 | — | 1.0 |
| L-ascorbic acid 2-glucoside | 1.0 | — | — | — | — |
| Stabilizer/fragrance | s.a. | s.a. | s.a. | s.a. | s.a. |
| Total | 100.0 | 100.0 | 100.0 | 100.0 | 100.0 |

The invention claimed is:

1. An oil in water emulsion cosmetic, comprising:
   (A) 0.3% to 1.0% by mass, relative to the mass of the cosmetic, of one or more selected from the group consisting of acrylates/steareth-20 methacrylate copolymer, acrylates/steareth-25 methacrylate copolymer, acrylates/steareth-20 methacrylate crosspolymer and ammonium acryloyldimethyltaurate/beheneth-25 methacrylate crosspolymer;
   (B) 1.0 to 30% by mass, relative to the mass of the cosmetic, of an ultraviolet protectant including an ultraviolet scattering agent;
   (C) 0.3% to 2.0% by mass, relative to the mass of the cosmetic, of a hydrophilic non-ionic surfactant having an HLB of 12.5 or higher which is one or more selected from the group consisting of polyoxyethylene (10-50) behenyl ether, polyoxyethylene (20-60) sorbitan monostearates, polyoxyethylene (10-50) polyoxypropylene (2-30) cetyl ethers and polyoxyethylene (20-100) hydrogenated castor oils;
   (D) 0.2% to 3.0% by mass, relative to the mass of the cosmetic, of a higher alcohol; and
   (E) water;
   wherein the cosmetic comprises an aggregate having a lamellar liquid-crystal structure which is formed by the (C) non-ionic surfactant, the (D) higher alcohol and the (E) water,
   wherein the ultraviolet scattering agent is present in the oil phase,
   wherein the molar ratio of non-ionic surfactant to higher alcohol, (C)/(D), is 0.1 to 0.5, and
   wherein the cosmetic maintains a bavarois-like texture and form.

2. The cosmetic, according to claim 1, wherein:
   the component (B) comprises a solid oil-soluble ultraviolet absorbing agent.

3. The cosmetic, according to claim 1, wherein the component (A) is acrylates/steareth-20 methacrylate copolymer.

* * * * *